(12) United States Patent
Dubald et al.

(10) Patent No.: US 11,229,597 B2
(45) Date of Patent: Jan. 25, 2022

(54) TOPICAL DOXYCYCLINE COMPOSITION

(71) Applicants: HORUS PHARMA, Saint-Laurent-du-Var (FR); UNIVERSITE CLAUDE BERNARD LYON 1, Villeurbanne (FR); CENTRE NATIONAL DE LA RECHERCHE SCIENTIFIQUE, Paris (FR)

(72) Inventors: Marion Dubald, Villeurbanne (FR); Sandrine Bourgeois, Lyons (FR); Hatem Fessi, Villeurbanne (FR); Martine Claret, Saint Sulpice (CH)

(73) Assignees: HORUS PHARMA, Saint-Laurent-du-Var (FR); UNIVERSITE CLAUDE BERNARD LYON 1, Villeurbanne (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 47 days.

(21) Appl. No.: 16/498,323

(22) PCT Filed: Apr. 3, 2018

(86) PCT No.: PCT/EP2018/058447
§ 371 (c)(1),
(2) Date: Sep. 26, 2019

(87) PCT Pub. No.: WO2018/185078
PCT Pub. Date: Oct. 11, 2018

(65) Prior Publication Data
US 2021/0100739 A1  Apr. 8, 2021

(30) Foreign Application Priority Data
Apr. 3, 2017 (FR) ...................... 1752853

(51) Int. Cl.
| | | |
|---|---|---|
| *A61K 9/00* | (2006.01) |
| *A61K 9/107* | (2006.01) |
| *A61K 47/44* | (2017.01) |
| *A61K 47/14* | (2017.01) |
| *A61K 47/40* | (2006.01) |
| *A61K 47/10* | (2017.01) |
| *A61K 31/65* | (2006.01) |

(52) U.S. Cl.
CPC .......... *A61K 9/0048* (2013.01); *A61K 9/0014* (2013.01); *A61K 9/107* (2013.01); *A61K 31/65* (2013.01); *A61K 47/10* (2013.01); *A61K 47/14* (2013.01); *A61K 47/40* (2013.01); *A61K 47/44* (2013.01)

(58) Field of Classification Search
CPC .......... A61K 9/00; A61K 9/107; A61K 47/44; A61K 47/14; A61K 47/40; A61K 31/65
See application file for complete search history.

(56) References Cited

U.S. PATENT DOCUMENTS
2006/0172982 A1  8/2006  Gardner

FOREIGN PATENT DOCUMENTS
| | | |
|---|---|---|
| CN | 106539817 A | 3/2017 |
| RU | 2095065 C1 | 11/1997 |
| WO | 2017035665 A1 | 3/2017 |

*Primary Examiner* — Zohreh A Fay
(74) *Attorney, Agent, or Firm* — BCF LLP

(57) ABSTRACT

The present invention relates to a novel pharmaceutical composition comprising doxycycline for topical application, in particular to the eye and eyelids. The invention also relates to this topical composition for use in the treatment of bacterial infections of the skin and mucous membranes.

13 Claims, 2 Drawing Sheets

TOPICAL DOXYCYCLINE COMPOSITION

FIELD OF THE INVENTION

The present invention relates to a novel pharmaceutical composition comprising doxycycline for topical application, in particular to the eye and eyelids. The invention also relates to this topical composition for use in the treatment of bacterial infections of the skin and mucous membranes.

STATE OF THE ART

Doxycycline is a tetracycline antibiotic which is mainly administered per os in pharmaceutical compositions adapted for such administration, essentially tablets of different forms with different dosages of doxycycline. There is also a liquid form suitable for administration as an intravenous infusion. The active principle is used as hyclate or monohydrate.

There are no commercial formulas suitable for topical administration of the product, mainly for problems of stability and preservation of the active principle in such compositions. Indeed, pharmaceutical compositions suitable for topical application must meet strict specifications as to their preservation, so that the product undergoes little degradation (usually less than 5%) when stored for 6 months or even up to 2 years. However, doxycycline degrades on contact with water, making it unsuitable for use in the form of conventional topical formulations.

The only topical applications of doxycycline reported in the literature are extemporaneous forms containing large amounts of antibiotics for very specific diseases. For example, application RU 2095065 discloses extemporaneous topical compositions with doxycycline contents above 1% for the treatment of ulcers and burns in leprosy patients. Application US 2006/0172982 discloses compositions with more than 10% doxycycline, up to 50%, to treat and prevent infections and inflammations (allergies, colds, etc.). Application CN 10653817 describes compositions with more than 2% doxycyciline, up to more than 20%, in powder form with particle sizes of more than 70 µm. These high levels correspond well to extemporaneous formulations, for which the shelf life is short, the high content acting to compensate for the loss of active principle.

The invention allows a novel solution for the treatment of bacterial infections of the mucous membranes and skin with a topical doxycycline composition that is stable over time.

DISCLOSURE OF THE INVENTION

To solve the problem of doxycycline stability, the invention relates to an anhydrous pharmaceutical composition for topical application of doxycycline, characterised in that it comprises:
  a) an anhydrous vehicle suitable for topical application which consists of a semi-solid hydrophobic material a1) selected from petrolatum alone or with lanolin added, optionally mixed with a liquid hydrophobic material a2) selected from paraffin, saturated di- or tri-esters of C6-C12 fatty acids, and
  b) doxycycline in a form suitable for application to the skin or mucous membranes.

Preferably, the doxycycline in a form suitable for application to the skin or mucous membranes is a doxycycline salt selected from doxycycline hyclate and doxycycline monohydrate, preferably doxycycline hyclate.

The doxycycline, in particular hyclate or monohydrate, preferentially hyclate, can be b1) in powdery or micronised solid form or in solution b2) in an anhydrous polyol, preferably in liquid form at room temperature (15° C.-25° C.) selected from glycerol, propylene glycol, triethylene glycol, butylene glycol, methylene glycol and polyethylene glycols of molecular weight from 200 to 1500 and mixtures thereof.

The concentration of doxycycline, in particular hyclate, is between 0.001% and 1% (m/m), preferably between 0.005% and 0.5% (m/m), more preferentially between 0.01% and 0.1% (m/m).

The invention also relates to this topical composition for use in the treatment of bacterial infections of the mucous membranes and skin.

DETAILED DESCRIPTION OF THE INVENTION

Figure 1:
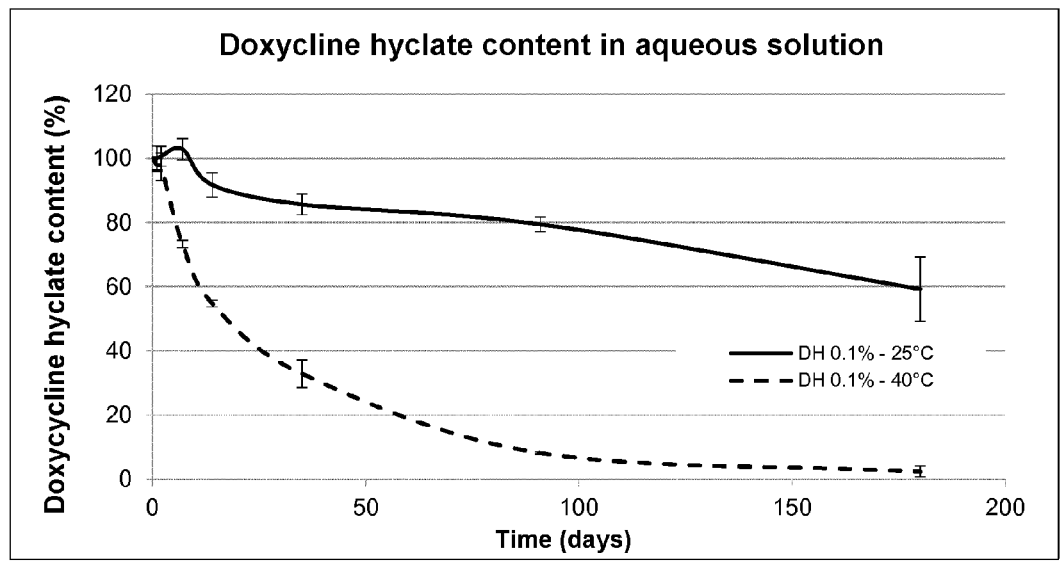
FIG. 1 shows a stability curve of 0.1% doxycycline hyclate in aqueous solution as a function of time at 25° C. and at 40° C.

The composition according to the invention is a pharmaceutical composition, i.e. a composition intended to be administered to a human or to an animal, and therefore meets the internationally recognised health requirements for the design and preparation of these compositions. In particular, excipients, their use and methods of analysis are known to the skilled person in the pharmaceutical field, and in particular comply with the requirements of the pharmacopoeia, such as the European Pharmacopoeia (Ph. Eur.), the U.S. Pharmacopeial Convention (USP) and the Japanese Pharmacopoeia (JP) in force.

The composition according to the invention is an anhydrous composition in order to limit the risks of degradation of the active principle. To this end, the components of the composition are anhydrous, i.e. with a residual moisture content of less than 0.5%, preferably less than 0.2% measured according to the method of determination indicated by the European Pharmacopoeia in force such as the Karl Fischer method for example.

The composition according to the invention is suitable for topical application, i.e. for direct application to the skin and/or mucous membranes. In particular, the composition according to the invention is an ophthalmic composition, intended to be applied to the eye, to the ocular mucosa or near the eye, to the eyelids, where the product can migrate to the eye and the ocular mucosa. For an ophthalmic composition, particular attention is paid to the choice of excipients, their qualities and methods of preparation to avoid the risk of microbial contamination and/or side effects such as eye irritation due to the fragility of the eye and ocular mucosa.

The composition according to the invention is also suitable for packaging in conventional containers for topical pharmaceutical compositions, and in particular for ophthalmic compositions, in particular tubes or vials. The packaging is suitable for single-dose or multi-dose uses, possibly with or without means of dosing the quantities applied. After packaging, the composition according to the invention can be stored for several months without substantial degradation of doxycycline.

The semi-solid hydrophobic material a1) is advantageously chosen from petrolatum, also known as vaseline or petroleum jelly, alone or with lanolin added in proportions customary to the skilled person. The petrolatum/lanolin mixture is also called lanovaseline, in which lanolin can represent up to 50% of the total weight of the mixture, generally in the range of 20 to 30%.

According to a preferred embodiment of the invention, the semi-solid hydrophobic material a1) is vaseline.

The liquid hydrophobic material a2) is selected from paraffin, di- or tri-esters of C6-C12 fatty acids, their mixtures and derivatives. These products used in pharmacy are well known to the skilled person. Saturated di- or tri-esters of fatty acids are esters of diols or of triols for which hydroxyls are esterified with a fatty acid. Particular mention may be made of medium-chain triglycerides (MCTs) such as glycerine and capric and caprylic acid triesters, in particular marketed under the names Miglyol® 810 or 812 or Labrafac® Lipophile. Mention may also be made of synthetic products such as polyoxyethylene C6-C12 fatty acid esters marketed under the name Labrasol®.

According to a particular embodiment of the invention, the liquid hydrophobic material a2) is paraffin.

The mass ratio of liquid hydrophobic material to semi-solid hydrophobic material preferably ranges from 50/50 to 0/100. The content of liquid hydrophobic material a2) in the mixture will depend on the properties sought for the final composition, in particular its viscosity and ease of use, depending on whether an application to the skin or mucous membranes, for example, is sought, or on the time during which the composition must be maintained in contact with the skin or mucous membranes.

The skilled person will be able to determine this content of liquid hydrophobic material a2) also taking into account the form of doxycycline that will be used. Preferably, the doxycline is in the form of a doxycycline salt selected from doxycycline hyclate and doxycycline monohydrate, preferably doxycycline hyclate.

According to a first embodiment of the invention, the doxycycline, in particular the doxycycline hyclate, is in the form of solid particles b1) of a size suitable for ophthalmic ointments. Advantageously, the particle size is less than or equal to 20 µm. This particle size is measured according to the usual methods of particle analysis described in the European Pharmacopoeia in force, such as laser diffraction particle size analysis. The final concentration of doxycycline in particulate form in the composition, in particular hyclate, is between 0.001% and 1% (m/m), preferably between 0.005% and 0.5% (m/m), more preferentially between 0.01% and 0.1% (m/m).

In this case, the anhydrous vehicle suitable for topical application will advantageously consist of a mixture of liquid hydrophobic material/semi-solid hydrophobic material with a mass ratio ranging from 50/50 to 10/90.

According to a second embodiment of the invention, the doxycycline, in particular the doxycycline hyclate, is in the form of a solution b2) in an anhydrous polyol. These anhydrous polyols described in the pharmacopoeias are advantageously chosen from glycerol, propylene glycol, polyethylene glycols with molecular weights ranging from 200 to 1500 and mixtures thereof.

The polyethylene glycols with molecular weights ranging from 200 to 1500 are advantageously chosen from Macrogols 400, 600 and 1500.

According to a preferred embodiment of the invention, the polyol is glycerol.

Preferably, the concentration of doxycycline, in particular of doxycycline hyclate in the polyol, ranges from 0.001% to 3.0% by mass based on the total mass of the solution.

The solution of doxycycline, in particular of doxycycline hyclate in the polyol may also include one or more cyclodextrins. Cyclodextrins in pharmacopoeias are well known to the skilled person. Particular mention may be made of α-cyclodextrins, β-cyclodextrins and hydroxypropyl-β-cyclodextrins.

In this case, the concentration of cyclodextrins in the polyol may advantageously range from 0.01% to 4.4% by mass based on the total mass of the solution.

According to a particular embodiment of the invention, the solution comprises:
from 0.03% to 2.0% (m/m) doxycycline, in particular doxycycline hyclate
from 0 to 4.4% (m/m) cyclodextrin, and
from 93.6% to 99.97% (m/m) polyol.

More particularly, the total doxycycline, in particular doxycycline hyclate, cyclodextrin and polyol represents 100% by mass of the solution, i.e. the solution consists only of doxycycline, polyol and, if need be, cyclodextrin.

Such a solution is prepared according to the usual methods of solution preparation.

Doxycycline, in particular doxycycline hyclate, is added to the polyol under magnetic stirring until it is completely dissolved. The resulting mixture is clear.

The preparation of cyclodextrin, in particular of doxycycline hyclate and of cyclodextrin, is carried out under the following conditions:
cyclodextrin is added to the polyol and magnetically stirred for 1 to 5 hours, preferably for 2 to 4 hours,
doxycycline is then added to the mixture and placed under magnetic stirring for 16 to 20 hours.

The resulting mixture is clear.

According to a preferred embodiment of the invention, the composition is a 'hydrophile-in-lipophile (H/L)' emulsion, the solution of doxycycline (b), in particular of doxycycline hyclate in the polyol forming globules surrounded by the anhydrous vehicle (a). The globules of polyol solution have a size less than or equal to 50 µm, advantageously between 20 and 30 µm.

The final concentration of doxycycline, in particular hyclate, in the form of a solution in an anhydrous polyol in the topical composition according to the invention, in particular in the form of an emulsion, is between 0.001% and 1% (m/m), preferably between 0.005% and 0.5% (m/m), more preferentially between 0.01% and 0.1% (m/m).

The present invention also relates to the solution of doxycyline in a polyol as previously defined as such, in particular as a pharmaceutical composition or as an intermediate composition for the preparation of a pharmaceutical composition, more particularly for the preparation of a topical composition in the form of an H/L emulsion as described above and below.

Advantageously, the composition according to the invention is a preservative-free composition. Preservatives generally used in topical compositions (pharmaceuticals, cosmetics, etc.) to avoid contamination by germs are well known to the skilled person, and include quaternary ammoniums, particularly benzalkonium chloride, alkyl-dimethyl-benzylammonium, cetrimide, cetylpyridinium chloride, benzododecinium bromide, benzethonium chloride, cetalkonium chloride, mercurial preservatives, such as phenylmercuric nitrate/acetate/borate, thiomersal, alcoholic preservatives, such as ethanol, chlorobutanol, benzyl alcohol, phenylethanol, phenylethyl alcohol, carboxylic acids, such as sorbic acid, phenols, in particular methyl/propyl paraben, amidines, for example chlorhexidine digluconate and/or chelating agents such as EDTA in combination with at least one other preservative.

According to the invention, 'preservative-free' means a composition substantially free of such preservatives to meet an indication of 'preservative-free'. Its preservative content is less than or equal to 10 ppm, more particularly less than or equal to 1 ppm, preferentially equal to 0 ppm, with no preservatives included in its composition.

In the absence of preservatives, the composition must undergo special treatment during its preparation and packaging in order to avoid and prevent contamination by microorganisms (such as Staphylococcus epidermidis), Staphylococcus aureus, Streptococcus pneumoniae, pneumococci, Streptococcus faecalis, Pseudomonas aeruginosa, Serratia marcescens, Klebsiella pneumoniae, Moraxella, Corynebacterium, Acinetobacter, Escherichia coli, Haemophilus influenzae). These treatments and procedures are well known to the skilled person. In this sense, a preservative-free composition according to the invention is distinguished from a simple composition comprising the same ingredients obtained without showing any particular precautions or describing steps of the process to obtain the sterility characteristic of compositions according to the invention, in particular ophthalmic compositions.

In particular, the invention relates to the following topical compositions:

| Hydrophobic ointment | % total mass of the composition |
|---|---|
| Vehicle | |
| Semi-solid hydrophobic material* | 50.000-90.000% |
| Liquid hydrophobic material* | 50.000-9.999% |
| Solid active principle | |
| Micronised doxycycline* | 0.001-1.000% |

*As defined above

| H/L emulsion | % total mass of the composition |
|---|---|
| Hydrophobic phase | |
| Semi-solid hydrophobic material* | 84.500-94.999% |
| Liquid hydrophobic material* | 0.000-9.500% |
| Hydrophilic phase | |
| Doxycycline* | 0.001-1.000% |
| Polyol* | 5.000% |

*As defined above

| H/L emulsion | % total mass of the composition |
|---|---|
| Hydrophobic phase | |
| Semi-solid hydrophobic material* | 83.560-89.998% |
| Liquid hydrophobic material* | 0.000-5.000% |
| Hydrophilic phase | |
| Doxycycline* | 0.001-1.000% |
| Cyclodextrins | 0.001-0.440% |
| Polyol* | 10.000% |

*As defined above

The preparation of compositions according to the invention are carried out according to the usual methods known to the skilled person, in particular with the precautions required to prepare sterile, preservative-free compositions and to package them.

The invention also relates to the use of a composition according to the invention for packaging in an appropriate pharmaceutical container to deliver the composition for topical application and storage for several months without substantial degradation of doxycycline.

The invention relates to a composition as defined above, for use in the treatment of bacterial infections of the mucous membranes or skin, in particular of the eyelids and/or the ocular mucosa.

The invention also relates to a method for treating bacterial infections of the mucous membranes or skin, in particular of the eyelids and/or the ocular mucosa, wherein an appropriate amount of composition according to the invention is applied at and/or near the place of infection and is allowed to act. The application will be repeated as necessary, advantageously until the symptoms of the infection disappear.

The composition will be advantageously used or the method will be advantageously implemented for conditions due to tetracycline sensitive bacteria, such as Staphylococcus epidermidis, Staphylococcus aureus, Streptococcus pneumoniae, pneumococci, Streptococcus faecalis, Pseudomonas aeruginosa, Serratia marcescens, Klebsiella pneumoniae, Moraxella, Corynebacterium, Acinetobacter, E. coli, Haemophilus influenzae for diseases such as stye, infectious conjunctivitis, infectious keratitis, blepharitis, meibomian gland dysfunction, iritis (anterior uveitis), canaliculitis and rosacea.

EXAMPLES

Materials and Methods

The different formulations are prepared using a vacuum mixer equipped with an adapted dispersion system.

The preparation in the form of a hydrophobic ointment containing the dispersed solid active principle is carried out according to the following method:

The liquid hydrophobic material/semi-solid hydrophobic material base is formulated by mixing in a water bath at 70° C. to make all components miscible.

The temperature of the mixture is lowered to 45° C. and the hydrophobic base is transferred to the mixer whose temperature is 45° C.

The doxycycline hyclate is added to the mixer and the whole is evacuated to 80%.

The formula is stirred for 30 minutes at 700 rpm at 45° C. and then the temperature of the entire mixture is reduced to 37° C.

The ointment obtained is packaged and cooled to room temperature.

The preparation in the form of an H/L emulsion containing the active principle in solution in the polyol is carried out according to the following method:

The liquid hydrophobic material/semi-solid hydrophobic material base (called phase A) is formulated by mixing in a water bath at 75° C. to make all components miscible. For the mass ratio of liquid hydrophobic material to semi-solid hydrophobic material 0/100, the semi-solid hydrophobic material is added directly to the mixer at 45° C.

The temperature of phase A is lowered to 45° C. and then phase A is transferred to the mixer whose temperature is 45° C.

The doxycyline hyclate is added to the polyol (called phase B) and magnetically stirred until it dissolves completely and then the temperature of the solution is increased to 45° C.

When phases A and B are at the same temperature, phase B is added to phase A under stirring to form an emulsion.

The emulsion is stirred for 30 minutes at 700 rpm at 45° C. and then the temperature of the entire mixture is reduced to 37° C.

The resulting emulsion is packaged and cooled to room temperature.

The preparation in the form of an H/L emulsion containing the active principle and cyclodextrins in solution in the polyol is carried out according to the following method:

The liquid hydrophobic material/semi-solid hydrophobic material base (called phase A) is formulated by mixing in a water bath at 75° C. to make all components miscible. For the mass ratio of liquid hydrophobic material to semi-solid hydrophobic material 0/100, the semi-solid hydrophobic material is added directly to the mixer at 45° C.

The temperature of phase A is lowered to 45° C. and then phase A is transferred to the mixer whose temperature is 45° C.

The cyclodextrin is added to the polyol (called phase B) and magnetically stirred then the doxycyline hyclate is added to phase B and magnetically stirred until all components are completely dissolved, the temperature of the solution is increased to 45° C.

When phases A and B are at the same temperature, phase B is added to phase A under stirring to form an emulsion.

The emulsion is stirred for 30 minutes at 700 rpm at 45° C. and then the temperature of the entire mixture is reduced to 37° C.

The resulting emulsion is packaged and cooled to room temperature.

In order to assay of the active principle in the formulation, the following extraction is carried out:
- 1.0 g of the formula is diluted in 10.0 g of water and stirred with a suitable stirring system for 30 minutes at 45° C.
- After filtration with a nylon filter at 0.45 µm, a dilution in the mobile phase is performed for a high-performance liquid chromatography assay.

The active principle content is determined by the following high-performance liquid chromatography method:
- Column: XTerra® RP 8 5 µm 4.6×250 mm
- Mobile phase:
  - 65% water containing 0.13% oxalic acid
  - 22% acetonitrile
  - 13% methanol
- Flow rate: 1.0 mL/min Stability Tests Stability tests are performed at temperatures of 25° C. and 40° C.:

In 0.1% aqueous solution, doxycycline is rapidly degraded as shown in FIG. 1.

Figure 2:
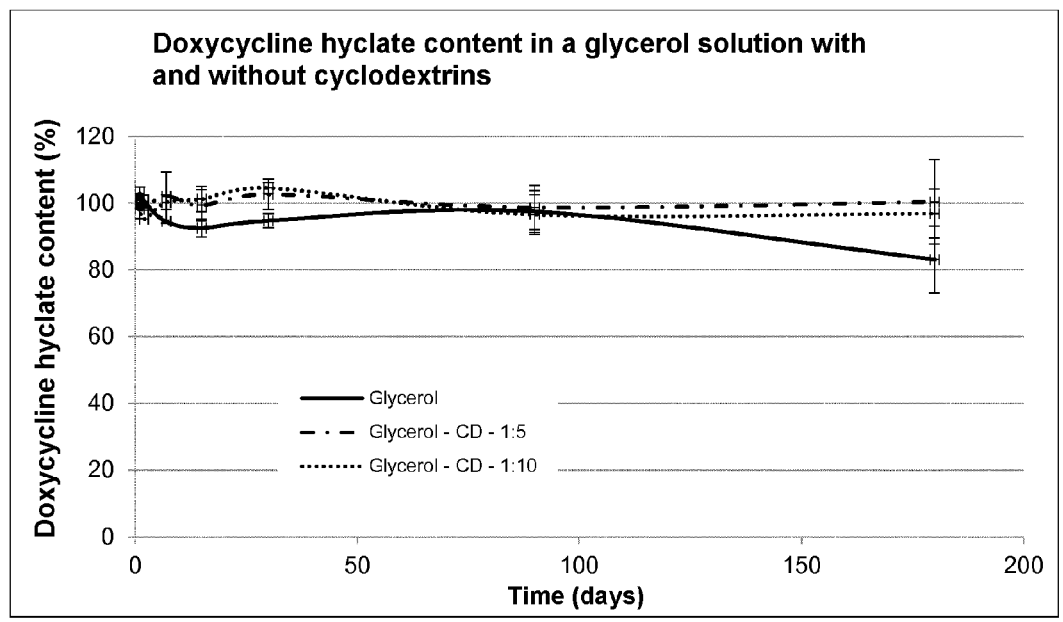
FIG. 2 shows a stability curve of 0.1% doxycycline hyclate, in glycerol solution with or without cyclodextrin, as a function of time at 25° C.

In glycerol (0.1% doxycycline hyclate) with and without β-cyclodextrins, the compositions according to the invention mark their high stability with no or little degradation of doxycycline (taking into account the margins of error of the measurements), as shown in FIG. 2.

Figure 3:
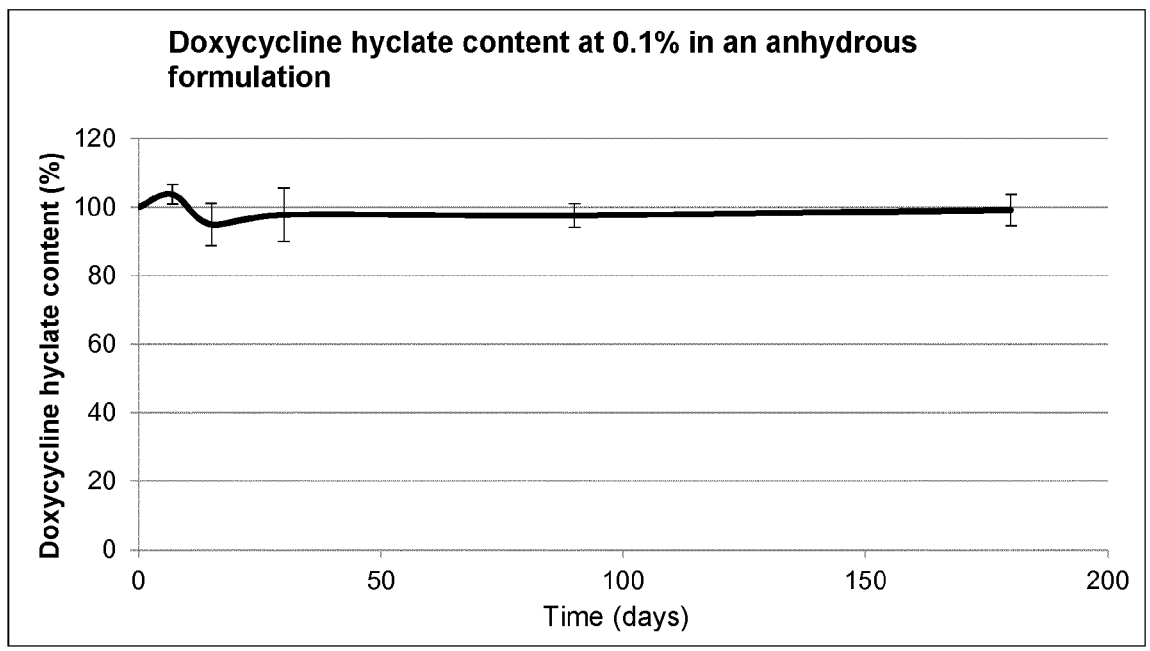
FIG. 3 shows a stability curve of an anhydrous formulation of 0.1% doxycycline hyclate in the presence of cyclodextrin as a function of time at 25° C.

In the topical formulation at 25° C. according to the invention, an anhydrous formulation at 0.1% doxycycline hyclate, as shown in FIG. 3.

Particular Compositions

For the preparation of the compositions below, white petroleum jelly (petrolatum) is used as a semi-solid hydrophobic material and liquid paraffin as a liquid hydrophobic material.

| Hydrophobic ointment | Weighed mass | % total mass of the composition |
|---|---|---|
| Vehicle | | |
| Semi-solid hydrophobic material | 450.000 g | 70.000% |
| Liquid hydrophobic material | 49.900 g | 29.900% |
| Dispersed solid active principle | | |
| Micronised doxycycline hyclate | 0.500 g | 0.100% |

| Emulsion 1 | Weighed mass | % total mass of the composition |
|---|---|---|
| Hydrophobic phase | | |
| Semi-solid hydrophobic material | 427.000 g | 85.400% |
| Liquid hydrophobic material | 47.500 g | 9.500% |
| Hydrophilic phase | | |
| Doxycycline hyclate | 0.500 g | 0.100% |
| Polyol | 25.000 g | 5.000% |

| Emulsion 2 | Weighed mass | % total mass of the composition |
|---|---|---|
| Hydrophobic phase | | |
| Semi-solid hydrophobic material | 474.500 g | 94.900% |
| Hydrophilic phase | | |
| Doxycycline hyclate | 0.500 g | 0.100% |
| Polyol | 25.000 g | 5.000% |

| Emulsion 3 | Weighed mass | % total mass of the composition |
|---|---|---|
| Hydrophobic phase | | |
| Semi-solid hydrophobic material | 448.200 g | 89.640% |
| Hydrophilic phase | | |
| Doxycycline hyclate | 0.150 g | 0.030% |
| β-Cyclodextrin | 1.650 g | 0.330% |
| Polyol | 50.000 g | 10.000% |

| Emulsion 4 | Weighed mass | % total mass of the composition |
| --- | --- | --- |
| Hydrophobic phase | | |
| Semi-solid hydrophobic material | 448.400 g | 89.680% |
| Hydrophilic phase | | |
| Doxycycline hyclate | 0.500 g | 0.100% |
| β-Cyclodextrin | 1.100 g | 0.220% |
| Polyol | 50.000 g | 10.000% |

| Emulsion 5 | Weighed mass | % total mass of the composition |
| --- | --- | --- |
| Hydrophobic phase | | |
| Semi-solid hydrophobic material | 447.300 g | 89.460% |
| Hydrophilic phase | | |
| Doxycycline hyclate | 0.500 g | 0.100% |
| β-Cyclodextrin | 2.200 g | 0.440% |
| Polyol | 50.000 g | 10.000% |

The invention claimed is:

1. An anhydrous pharmaceutical composition for topical application of doxycycline comprising:
    a) an anhydrous vehicle suitable for topical application consisting of a semi-solid hydrophobic material a1) selected from petrolatum alone or with lanolin added, optionally mixed with a liquid hydrophobic material a2) selected from paraffin, saturated di- or tri-esters of C6-C12 fatty acids, and
    b) doxycycline in a form suitable for application to the skin or mucous membranes selected from b1) a solid form of micronised powder with a particle size of 20 µm or less and b2) a form of solution in an anhydrous polyol,
    wherein the doxycycline is a doxycycline salt selected from doxycycline hyclate and doxycycline monohydrate, and the doxycycline content is between 0.001% and 1% (m/m),
    wherein the polyols are selected among glycerol, propylene glycol triethylene glycol, butylene glycol, methylene glycol and polyethylene glycols of molecular weight from 200 to 1500 and mixtures thereof, and
    wherein the said composition during storage is stable for more than 150 days at 25° C.

2. The composition according to claim 1, wherein the doxycycline is in a solid form of micronised powder b1) and the mass ratio of liquid hydrophobic material to semi-solid hydrophobic material ranges from 50/50 to 10/90.

3. The composition according to claim 1, wherein the concentration of doxycycline in solution in the anhydrous polyol ranges from 0.001% to 3% by mass based on the total mass of the solution b2).

4. The composition according to claim 1, wherein the solution b2) in an anhydrous polyol comprises one or more cyclodextrins.

5. The composition according to claim 1, wherein the solution b2) comprises:
    from 0.03% to 2.0% (m/m) doxycycline hyclate
    from 0 to 4.4% (m/m) cyclodextrin, and
    from 93.6% to 99.97% (m/m) polyol.

6. The composition according to claim 1, wherein it is a 'hydrophile-in-lipophile (H/L)' emulsion, the doxycycline-in-polyol solution b2) forming globules surrounded by the anhydrous vehicle.

7. The composition according to claim 6, wherein the globules of polyol solution b2) have a size of 50 µm or less.

8. The composition according to claim 7, wherein the globules of polyol solution b2) have a size between 20 and 30 µm.

9. The composition according to claim 1, wherein the doxycycline is in the form of a solution in an anhydrous polyol and the mass ratio of paraffin to petrolatum ranges from 50/50 to 0/100.

10. The composition according to claim 1, wherein the doxycycline content is between 0.01% and 0.1% (m/m).

11. A method for treating bacterial infections of the mucous membranes or skin of a patient in need thereof, comprising applying the composition according to claim 1 at and/or near the place of infection.

12. The method according to claim 11, wherein the bacterial infections of the mucous membranes or skin are selected among stye, infectious conjunctivitis, infectious keratitis, blepharitis, meibomian gland dysfunction, iritis (anterior uveitis), canaliculitis and rosacea.

13. The method of claim 11, wherein the mucous membranes or skin is selected among the eyelids and the ocular mucosa.

* * * * *